US006572538B2

(12) United States Patent
Takase

(10) Patent No.: US 6,572,538 B2
(45) Date of Patent: Jun. 3, 2003

(54) FLEXIBLE ENDOSCOPE

(75) Inventor: Seisuke Takase, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/908,014

(22) Filed: Jul. 18, 2001

(65) Prior Publication Data

US 2002/0032368 A1 Mar. 14, 2002

(30) Foreign Application Priority Data

Jul. 28, 2000 (JP) ........................................ 2000-229510

(51) Int. Cl.[7] ................................................ A61B 1/00
(52) U.S. Cl. ...................................... 600/144; 600/139
(58) Field of Search ................................ 600/139, 140, 600/144, 146

(56) References Cited

U.S. PATENT DOCUMENTS

| | | | | | |
|---|---|---|---|---|---|
| 3,854,473 A | * | 12/1974 | Matsuo | ................... | 128/207.14 |
| 3,948,251 A | * | 4/1976 | Hosono | ....................... | 600/144 |
| 4,329,980 A | * | 5/1982 | Terada | ......................... | 600/140 |
| 4,690,175 A | * | 9/1987 | Ouchi et al. | ................ | 138/151 |
| 4,893,613 A | * | 1/1990 | Hake | ........................... | 600/144 |
| 4,899,787 A | * | 2/1990 | Ouchi et al. | ................ | 138/131 |
| 4,977,887 A | * | 12/1990 | Gouda | ......................... | 600/140 |
| 5,025,778 A | * | 6/1991 | Silverstein et al. | ......... | 600/104 |
| 5,125,395 A | * | 6/1992 | Adair | .......................... | 600/104 |
| 5,733,245 A | * | 3/1998 | Kawano | ..................... | 600/139 |
| 5,885,208 A | * | 3/1999 | Moriyama | ................. | 600/144 |
| 6,083,152 A | * | 7/2000 | Strong | ........................ | 600/121 |
| 6,203,494 B1 | * | 3/2001 | Moriyama | ................. | 600/144 |

FOREIGN PATENT DOCUMENTS

| | | |
|---|---|---|
| JP | 2-283346 | 11/1990 |
| JP | 6-269397 | 9/1994 |
| JP | 8-136823 | 5/1996 |

* cited by examiner

Primary Examiner—Linda C. M. Dvorak
Assistant Examiner—Kenneth G Schopfer
(74) Attorney, Agent, or Firm—Scully, Scott Murphy & Presser

(57) ABSTRACT

The endoscope comprises a flexible insertion member with different hardness for bending in a predetermined area of longitudinal direction thereof. This insertion member includes a flexible tube having resin sheathing layer on the outside and slender inner parts passing through the flexible tube. An amount of change in hardness level for bending of the inner parts in a longitudinal direction is designed larger than an amount of change in hardness level for bending of the sheathing layer of the flexible tube in a longitudinal direction.

16 Claims, 4 Drawing Sheets

FLEXIBLE ENDOSCOPE

This application claims the benefit of Japanese Application No. 2000-229510 filed in Japan on Jul. 28, 2000, the contents of which are incorporated by this reference.

BACKGROUND OF THE INVENTION

1. Field of the Invention

The present invention relates to an endoscope having a flexible insertion member with different hardness for bending in a predetermined area of the longitudinal direction thereof.

2. Related Art Statement

Conventionally, wide use has been made of a medical endoscope capable of observing organs in a body cavity or conducting various medical treatments using a therapeutic instrument passed through a therapeutic instrument channel, if necessary, by inserting a slender insertion member into the body cavity.

The endoscope used in the medical field enables therapy or treatment by inserting the insertion member into a body cavity to observe organs or to conduct various medical treatments using the therapeutic instrument passed through a therapeutic instrument channel of the endoscope.

For example, an endoscope inserted into the colon requires the capability of ease of operation and flexibility to a large extent after inserting the insertion member. In other words, flexibility (softness) is required for the distal part of the insertion member to enable insertion along a bent passage. On the other hand, a predetermined amount of stiffness (also called hardness) is required for the proximal part of the insertion member after the operator inserts the distal part of the insertion member. Accordingly, there are endoscopes having various kinds of designs/devices on the resin of a sheathing member of the insertion member so as to be capable of performing these features.

For example, Japanese Laid-Open Patent Application (Tokukaihei) No. 2-283346 discloses a flexible tube for an endoscope at least containing the common polymer material in each layer of the double laminated polymer material layers of the sheathing member.

Endoscope devices used in the medical field have required cleaning and disinfection after an individual endoscopic examination and treatment to prevent infection among patients when re-using the device for other patients.

In recent years, the autoclave sterilization method (high pressure steam sterilization), which is not complicated and is capable of being used immediately after sterilization, and which is inexpensive in terms of running costs is becoming the mainstream of the sterilization treatment for the disinfection of medical devices.

For example, Japanese Laid-Open Patent Application No.5-285103 discloses an autoclaving device for an endoscope which is capable of autoclave sterilization without deteriorating the function of the endoscope.

The environment of steam sterilization under pressure is extremely harsh for a precision electronic instrument such as endoscope. Therefore, to produce an endoscope being resistant to this condition, various measures relating to high pressure, high temperature, and steam are taken in comparison with a general purpose endoscope which is designed to be used in a general cleaning and disinfection manner.

However, in accordance with the flexible tube for the endoscope disclosed in the Japanese Laid-Open Patent Application 2-283346, the polymer resin of the sheathing member of an insertion member deteriorates by the heat generated upon steam sterilization of the endoscope under pressure. Also, the problem arises that the resin of the sheathing member of the flexible tube for the endoscope is subject to deterioration and alteration over time.

Furthermore, once the resin of the sheathing member deteriorates, the stiffness for bending of the insertion member in a predetermined length of longitudinal direction is altered compared with the initial state. As a result, a problem arises in that it becomes hard for users to appropriately insert.

SUMMARY OF THE INVENTION

The object of present invention is to provide an endoscope capable of being inserted smoothly for an extended period, even if the sheathing member layer has deteriorated or become altered after extended use or after repetitive steam sterilization of the endoscope under high pressure.

Briefly, the present invention relates to a flexible endoscope comprising a flexible insertion member having different hardness in bending in a predetermined area in the longitudinal direction. This insertion member includes a flexible tube having a resin sheathing layer on the outside and slender inner parts passing through the flexible tube. An amount of change in the hardness level for bending the inner parts in the longitudinal direction is designed to be larger than an amount of change in the hardness level for bending the sheathing layer of the flexible tube in the longitudinal direction so as to maintain the ability to insert the endoscope smoothly for extended periods of time, even after the sheathing layer has deteriorated or become altered.

BRIEF DESCRIPTION OF THE DRAWINGS

FIG. 1 is a diagram for explaining the entire configuration of an endoscope device.

FIG. 2 is a diagram for explaining the configuration of a flexible tube.

FIG. 3 is a diagram for explaining the flexible tube and inner parts of an insertion member.

FIG. 4 is a diagram for explaining one example of the configuration of an inner part, a stilet.

FIG. 5 is a diagram for explaining another example of the configuration of a stilet.

FIG. 6 is a diagram for explaining still another example of the configuration of a stilet.

FIG. 7 is a diagram for explaining one example of the configuration of an inner part, a wire coating coil.

FIG. 8 is a diagram for explaining another example of the configuration of a wire coating coil.

DETAILED DESCRIPTION OF THE PREFERRED EMBODIMENTS

The construction of the present invention is explained hereafter, with reference to the embodiments.

The first embodiment of the present invention is explained hereafter, with reference to FIG. 1 to FIG. 6.

Figure 1:
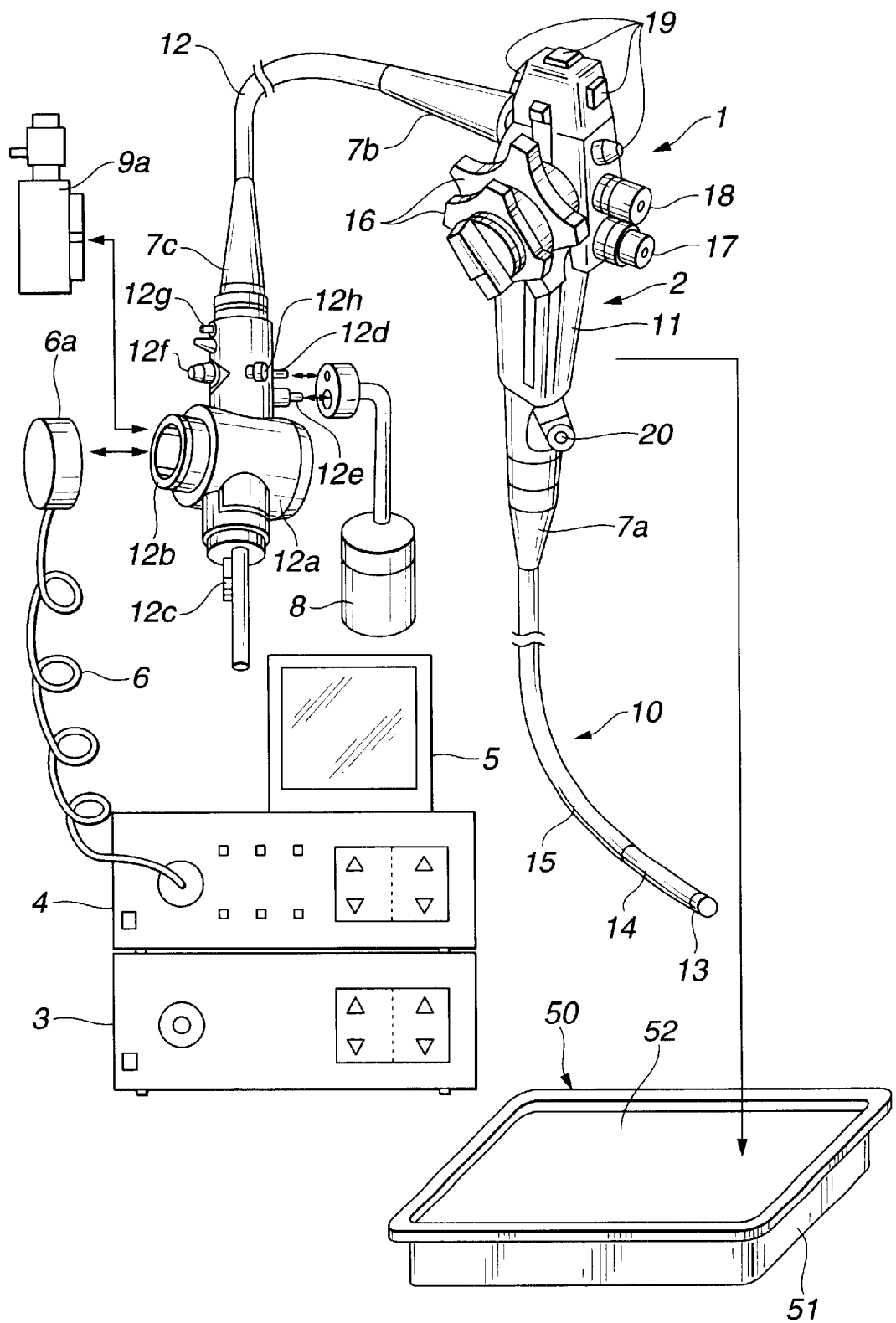
FIG. 1 to FIG. 6 are diagrams for explaining the first embodiment of the present invention.

As shown in FIG. 1, the endoscope device 1 of the present embodiment mainly comprises an electronic endoscope (referred to as endoscope hereafter) 2, a light source device 3, a video processor 4 and a monitor 5.

Endoscope 2 has an imaging means, for which the light source device 3 provides light. The video processor 4 controls the imaging means as well as processing image signals obtained by the imaging means for video signals, for example. The monitor 5 is connected to the video processor 4. In addition, the numeral 50 indicates a storage case for the endoscope 2 during sterilization described later.

Endoscope 2 comprises an insertion member 10, a control section 11, and a universal cord 12. The insertion member 10 is elongated and flexible. The control section 11 is connected to the proximal end of the insertion member 10. The universal cord 12 is flexible, and is elongated from the side of the control section 11.

At the end of the universal cord 12 is provided a connector 12*a*, which is detachably connected to the light source device 3. By connecting the connector 12*a* to the light source device 3, light from a lamp (not shown) attached on the light source device 3 is transferred to a light guide of the endoscope 2 (not shown) to lighten the area to be inspected.

At the connecting part between the insertion member 10 and the control section 11, an insertion member anti-breakage member 7*a* made of elastic material is placed to prevent abrupt bending. Also, at the connecting part between the control section 11 and the universal cord 12, a similar control section anti-breakage member 7*b* is provided. Furthermore, at the connecting part of the universal cord 12 and the connector unit 12*a*, a similar connector unit anti-breakage member 7*c* is provided.

The insertion member 10 of the endoscope 2 comprises a rigid part of distal end 13, a bending section 14, and a flexible tube 15 which is soft, and they are connected together in the order from the distal end to the proximate end.

The rigid part 13 of distal end is made of a hard material. On the top face of the rigid part 13, are placed, for example, an observation window (not shown), an illumination window, an air and water supplying nozzle to spray a cleaning liquid or gas to the observation window, and a suction port to aspirate body fluids, wastes and like.

The bending section 14 is formed with a plurality of small bending pieces (not shown) in the connection so as to be flexibly bent.

The flexible tube 15 has the delicate characteristics of being soft and elastic.

The control section 11 has an angling knob 16. By operating the angling knob 16 appropriately, the bending section 14 can be bent to any direction desired. In other words, by bending the bending section 14, the top face of the rigid part 13 including the observation window can be turned to the desired direction.

Furthermore, the control section 11 has an air and water supply operation button 17, an suction operation button 18, a plurality of remote switches 19, and a therapeutic instrument insertion port 20 besides the angling knob 16.

By appropriately operating the atmosphere and water supply operation button 17, the air and water supplying nozzle sprays with cleaning solution or gas. Also, by operating the suction operation button 18, body fluids and the like are aspirated through the suction port. A plurality of remote switches 19, for example, remotely controls the video processor 4. The therapeutic instrument insertion port 20 is connected to a therapeutic instrument channel tube placed inside of the insertion member of the endoscope 2, described later.

On the side of the connector 12*a* is provided an electric connector 12*b*, to which is detachably connected a signal connector 6*a* of a signal cord 6 connected to the video processor 4. By connecting the signal connector 6*a* to the video processor 4, the imaging means of the endoscope 2 is controlled, video signals are created from the image signals transmitted through the imaging means, and the endoscope observation image is displayed on the screen of the monitor 5.

On the electric connector 12*b*, is placed an air-vent (not shown) to connect the inside and the outside of the endoscope 2. Thus, the electronic connector 12*b* of the endoscope 2 has a freely-detachable water proof cap 9*a* with a pressure-regulating valve (hereinafter, referred to as water-proof cap) (not shown) for closing the air-vent.

The connector unit 12*a* has a gas supplying cap 12*c*, a water supplying tank pressure cap 12*d*, a liquid supplying cap 12*e*, a suction cap 12*f*, an injecting cap 12*g*, and a ground terminal cap 12*h*.

The gas supplying cap 12*c* is connected to a gas supplying source (not shown) built in the light source device 3 in a freely detachable manner. The water supplying tank pressure cap 12*d* and the liquid supplying cap 12*e* are connected to a water supplying tank 8 in a freely detachable manner. The suction cap 12*f* is connected to a suction source (not shown) to aspirate from the suction port. The injection cap 12*g* is connected to a water supply device (not shown) to supply water. The ground terminal cap 12*h* is connected to an electric cable. This allows feeding back high frequency leakage current generated during diathermy to a diathermy device (not shown).

After being used for observation and treatment, the endoscope 2 is designed to be capable of being cleaned and is resistant to steam sterilization under high pressure. Upon steam sterilization of the endoscope 2 under high pressure, the waterproof cap 9*a* is attached on the electronic connector 12*b*. Also, upon steam sterilization of the endoscope 2 under high pressure, the endoscope 2 is stored in the storage case for sterilization 50.

The storage case for sterilization 50 comprises a case body, a tray 51 and a lid member 52. The tray 51 includes a restricting part (not shown) to fit the shape of the endoscope to each part of the insertion member 10, the control section 11, the universal cord 12, the connector unit 12*a* and the like of the endoscope 2. Also, a plurality of air-vents are placed on the tray 51 and the lid member 52 to introduce high pressured steam into the case.

Also, the insertion member 10 has the advantage of being less stressful for a test subject for experiments when the insertion member 10 having a soft configuration over the whole-length is inserted into the body cavity. However, this leads to the deteriorated ability of the distal part of the insertion member to respond to manipulations such as twisting performed at the proximal part thereof, when the insertion member 10 has softness. Thus, the distal part of the insertion member 10 is designed to be soft, but the proximal part thereof is designed to be harder than the distal part.

The configuration of the flexible tube 15 is described in detail hereafter.

Figure 2:
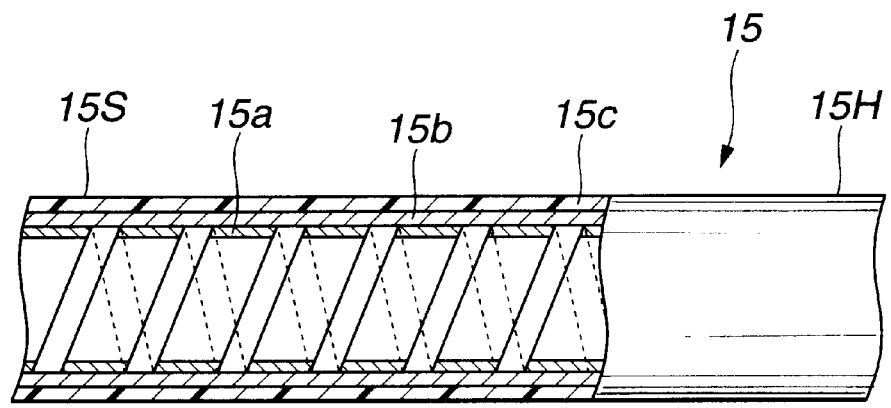

As shown in FIG. 2, the flexible tube 15 comprises a tube by laminating a spiral tube 15*a*, a braid 15*b* and a sheathing tube 15*c* in that order from the innermost layers.

Figure 3:
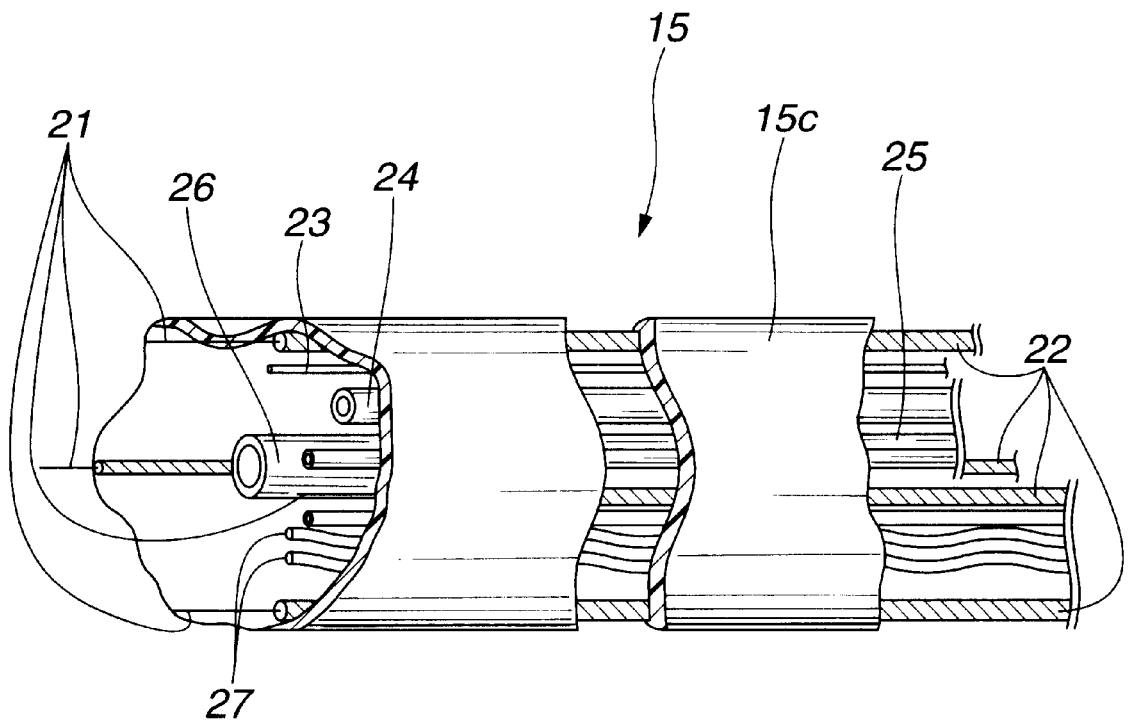

As shown in FIG. 3, various inner parts are passed through the inside of the flexible tube 15. The spiral tube 15*a* is made by spirally winding thin-stripped metal part. The braid 15*b* is made by weaving metal wires or non-metal wires. The sheathing tube 15*c* is an outermost housing layer made of resin material.

As resin materials composing the sheathing tube 15c, use is made of an ester thermoplastic elastomer, an amide thermoplastic elastomer, a styrene resin, an olefin resin, a fluorine rubber, a silicone rubber, or an appropriate mixture of these materials.

Material of the sheathing tube 15c is selected in accordance with the desire of the user in consideration of its performance such as durability, ability of insertion and like and chemical resistance during cleaning and sterilization.

Also, the hardness of the sheathing tube 15c is designed to be soft at the distal part of the insertion member 10, but the proximal part is designed to be harder than the distal part. Thus, the insertion member 10 is designed to have different hardness in the predetermined areas in the longitudinal direction.

In the present embodiment, the sheathing tube 15c of a soft part positioned on the distal part (hereafter abbreviated as soft part of the tube 15S) and a hard part positioned on the proximate part, which is flexible, but harder than the soft part of the tube 15S (hereafter abbreviated to hard part of the tube 15H). In addition, an amount of change in hardness of the soft part of the tube 15S and the hard part of the tube 15H of the sheathing tube 15c is shown as the difference (X) in the hardness of the tube.

Also, the hardness described here refers to the stiffness upon bending to a predetermined extent in the longitudinal direction of the flexible tube 15. Furthermore, the predetermined extent of bending means the power required to bend at least a part of the flexible tube 15 to the extent, for example, of being an arc-shape having a diameter of 20 cm. The arc-shape having a diameter of 20 cm is the extent, for example, that the insertion member 10 of the endoscope 2c is inserted to reach the appendix of the colon without loosing.

Also, as the resin material for the sheathing tube 15c, for example, thermosetting resin which become hard in response to the heat-loading temperature during steam sterilization under high pressure, or a urethane resin having a lower softening temperature than the heat-loading temperature during steam sterilization under high pressure or having low critical temperature to maintain the function of an endoscope, are not suitable as resin material to compose the sheathing tube 15c, and shall not be selected.

As shown in FIG. 3, a bending wire 21, a wire coating coil 22, a stilet 23, a light guiding 24, an air and water supplying tube 25, a therapeutic instrument channel tube 26, a signal cable 27 and like are passed through the inside of the flexible tube 15.

As to the bending wire 21, for example, four bending wires 21 are passed as shown. They move back and forth by the operation of the angling knob 16 to bend the bending section 14 in a predetermined direction. The wire coating coil 22 should cover each bending wire 21 to fit together in such a manner that there is play between them. The stilet 23 is a flexibility adjustor to adjust the hardness of a predetermined area in the longitudinal direction of the flexible tube 15. The light guide 24 is a guide to provide light. The air and water supplying tube 25 and the therapeutic instrument channel tube 26 are made of a resin tube such as PTFE. In the signal cable 27, the outer packaging is coated with PFA and the like.

Figure 4:
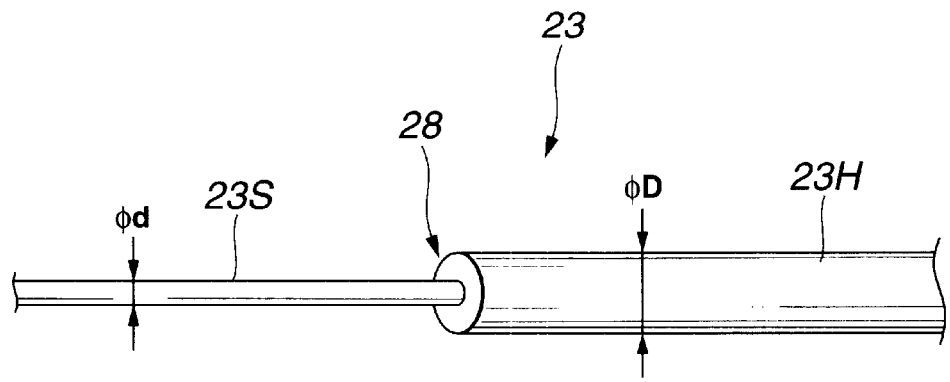

The stilet 23 is described hereafter, with reference to FIG. 4.

As shown in the figure, the stilet 23 is made of an elastic material such as superelastic alloy or stainless steel, e.g. SUS304. The stilet is designed to be soft at the distal part of the insertion member 10, but the proximal part is designed to be harder than the distal part. To alter the hardness in a predetermined area of the longitudinal direction, the diameter size is changed to a larger diameter for example, from $\phi d$ to $\phi D$.

In other words, the stilet 23 comprises the soft part of the stilet 23S positioned on the distal part with a smaller diameter ($\phi d$) and the hard part of the stilet 23H having a predetermined extent of stiffness and being positioned on the proximal part thereof with a larger diameter. This construction allows us to provide the distal part of the insertion member with flexibility and to provide the proximal part thereof with the desired hardness.

An amount of change in the hardness of the soft part of the stilet 23S and the hard part of the stilet 23H is indicated as the difference (Y) in the hardness of the stilet. The difference (Y) in the hardness of the stilet is designed to be greater than the difference (X) in the hardness of the tube.

One end or both ends of the stilet 23 is fixed to the proximal end of the bending section 14 or a metal connecting tube and like, embedded on the end of the flexible tube 15. Thus, when the insertion member 10 is moved during use, for cleaning and disinfection of the endoscope by users, the arrangement of this stilet 23 is not disturbed and thus may not damage and interfere with the movement of other inner parts, including the bending wire 21, the wire coating coil 22, the light guide 23, a air and water supplying tube 25, and a therapeutic instrument channel tube 26 and a signal cable 27 by pressing.

Furthermore, in the present embodiment shown in FIG. 3, a construction in which one stilet 23 is built into the inside of the flexible tube is shown, but another construction having a plurality of built-in stilets 23 may be used.

Also, in accordance with the present embodiment, the hardness of the sheathing tube 15c is designed to be varied according to the position in the longitudinal direction, but the same hardness over the entire length may be designed.

In this instance, typical conditions during the steam sterilization of an endoscope 2 under high pressure will be described.

As one of the conditions, there is an American Standard, ANSI/AAMI ST37-1992 that is approved by American National Standards Institute and issued by Association of American Medical Instruments.

According to this standard, a pre-vacuum type sterilization process requires a condition of 132° C. for four minutes, and a gravity type sterilization process requires 132° C. for ten minutes.

The temperature during the sterilization process of steam sterilization under high pressure depends on the type of steam sterilization under high pressure devices or the time of the sterilization process. Generally, the temperature is set to be within the range of between 115° C. to approximately 138° C. However, some types of sterilization devices are capable of being set up to approximately 142° C.

On the other hand, the time depends on the temperature condition of the sterilization process. In other words, generally, the time is set to the range between three minutes to sixty minutes. Furthermore, some types of sterilization devices are capable of being setting up to approximately 100 minutes.

The pressure inside the sterilizing chamber during the sterilization process is set to be approximately 0.2 MPa above the atmosphere pressure.

Next, the general process of the pre-vacuum type steam sterilization under pressure of the endoscope will be briefly described.

First of all, a waterproof cap 9a is attached on the electric connector 12b of the endoscope 2 to be sterilized. Next, the endoscope is stored in a sterilization storage case 50 to place the storage case 50 in a sterilizing chamber (not shown). Subsequently, the inside of sterilizing chamber before high pressured sterilization is turned into a pressure reduced state (also known as a pre-vacuum process).

By attaching the waterproof cap 9a on the electronic connector part 12b, a pressure-regulating valve is closed and subsequently the air-vent is closed. In other words, the inside and outside of the endoscope 2 are sealed in a watertight manner.

Furthermore, the pre-vacuum process is a process to infiltrate steam into the minute components of the device to be sterilized during the sterilization process. This process allows the device to spread high pressure high temperature steam on the entire device to be sterilized by reducing the pressure inside the sterilizing chamber. The pressure inside the sterilizing chamber during this pre-vacuum process is generally set to be approximately 0.07 to 0.09 MPa below the atmosphere pressure.

During the pre-vacuum process, the difference between the pressure inside and outside the endoscope 2 is generated because the outer pressure gets lower than the inside pressure of the endoscope 2 when the pressure of the sterilizing chamber is reduced.

Subsequently, the pressure-regulating valve of the waterproof cap 9a is opened and the inside and outside of the endoscope 2 become connected through an air-vent. This prevents the pressure difference between the inside and outside of the endoscope 2 from becoming larger. In other words, damage to the endoscope 2 caused by pressure difference is prevented.

Next, a sterilization process to send high pressure high temperature steam into the sterilizing chamber to sterilize it will be described.

In this sterilization process, the inside of the sterilizing chamber is pressurized. Subsequently, a pressure difference in which the outside pressure of the endoscope 2 becomes larger than inside pressure thereof is generated. Thus, the pressure-regulating valve of the waterproof cap 9a is closed. This shuts off high pressured steam from entering the endoscope through an air-vent.

However, high pressured steam slowly infiltrates into the inside of the endoscope 2 though the sheathing tube 15c of the flexible tube 15 made of polymer material, or an o ring (not shown) made of fluorine or silicone rubber that is a sealing means placed on the connecting part of an endoscope 2.

At this time, pressure is generated from the outside to the inside the endoscope 2 after adding the pressure reduced during the pre-vacuum process to the pressure pressurized during sterilization process.

Next, drying (drying process) is performed by reducing the pressure inside the endoscope again after the sterilization process in order to dry the sterilized device.

In this drying process, drying of the endoscope 2 in the sterilizing chamber is promoted by reducing the pressure inside the sterilizing chamber to eliminate steam from the sterilizing chamber. The pressure inside the sterilizing chamber during this drying process is generally set to approximately 0.07 to 0.09 MPa below the atmosphere pressure. Furthermore, the drying process is performed arbitrarily if necessary.

In the pressure reduction process after the sterilizing process, the pressure difference in which the outside pressure of the endoscope 2 becomes smaller than inside pressure thereof is generated by reducing the pressure inside of the sterilizing chamber. At almost the same time when the pressure difference is generated, the pressure-regulating valve of the waterproof cap 9a is opened and the inside and outside of the endoscope 2 become connected through an air-vent. This prevents the pressure difference between the inside and outside of the endoscope from becoming larger.

Subsequently, the pressure-regulating valve of the waterproof cap 9a is closed when the pressure reducing process is finished, the sterilizing chamber is pressurized, and the pressure difference is generated because the outside pressure of the endoscope 2 becomes larger than the inside pressure.

Furthermore, after the entire process of steam sterilization under high pressure is finished, the pressure from the outside to the inside is generated on the outer package of the endoscope 2 for the extent of pressure reduced in the pressure reducing process. Subsequently, when the waterproof cap 9a is removed from the electronic connector part 12b, the inside of the endoscope 2 is connected to the outside through an air-vent. This removes the load caused by the pressure difference generated on the outer package of the endoscope 2 as the pressure inside the endoscope becomes the same as the atmosphere pressure.

As described above, when the endoscope 2 is sterilized with a steam sterilization with a pressure device, the resin composing the sheathing tube 15c tends to alter by heat stress during the high temperature high pressured steam process.

In other words, the hardness of the sheathing tube 15c designed at room temperature is altered to reduce the hardness difference between the soft part of the tube 15S and the hard part of the tube 15H designed in the initial state. Thus, a predetermined difference (X) in hardness of the tube is not obtained in this state of the sheathing tube 15c.

On the other hand, for example, in the case of the stilet 23 made of superelastic alloy placed inside of the flexible tube 15, its size of outer diameter is altered in a predetermined area in the longitudinal direction. In other words, the stilet comprises the soft part of the stilet 23S and the hard part of the stilet 23H to create a difference (Y) in the hardness of the stilet. Thus, when the stilet is exposed to the high temperature, high pressured steam process, the difference (Y) in the hardness of the stilet will not be altered.

In other words, in accordance with the present embodiment, while the difference (X) in hardness of the tube is set on the sheathing tube 15c, and the difference (Y) in hardness of the stilet is set on the stilet 23, the relationship of Y>X is set between the difference (X) in hardness of the tube and the difference (Y) in hardness of the stilet. Thus, even if the resin of the sheathing tube 15c deteriorates by heat stress during the high temperature, high pressure steam process and thereby the difference (X) in the hardness of the tube becomes closer to 0, the hardness in a predetermined area of the longitudinal direction of the flexible tube 15 is maintained by the difference (Y) in the hardness of the stilet, which is generated by the soft part of the stilet 23S and the hard part of the stilet 23H of the stilet 23. In other words, the flexible tube 15 is capable of maintaining properties in which the distal part is soft, but the proximal part is still harder than the distal part even under the high temperature steam stress.

In this way, by designing the hardness level of the flexible tube composing the insertion member of the endoscope based on the difference in the hardness of the stilet placed as an inner part, and not based on the difference in the hardness of the tube, the hardness level possessed by the flexible tube is able to be maintained under high temperature steam stress during the high temperature high pressure steam process. This prevents deteriorating the ability to insert the insertion member after steam sterilization under high pressure.

Also, when the difference (X) in the hardness of the tube is set to X>0 at the initial state, the stilet also has a difference in hardness in the initial state. This makes clear the difference in the hardness of the insertion member, and various kinds of endoscope to be used for various purpose will be provided.

However, the clear difference in the hardness of the insertion member in the initial state is lost by high temperature steam stress after the repetition of the high temperature, high pressure steam process and deterioration over time.

To cope with this problem, when the difference (X) in hardness of the tube is set to X=0 at the initial state, regardless of the deterioration caused by the repetition of the high temperature, high pressure steam process and the deterioration of the resin of the sheathing tube over time, the balance between the soft part and the hard part of the insertion member in the initial stage is continuously maintained.

Figure 5:
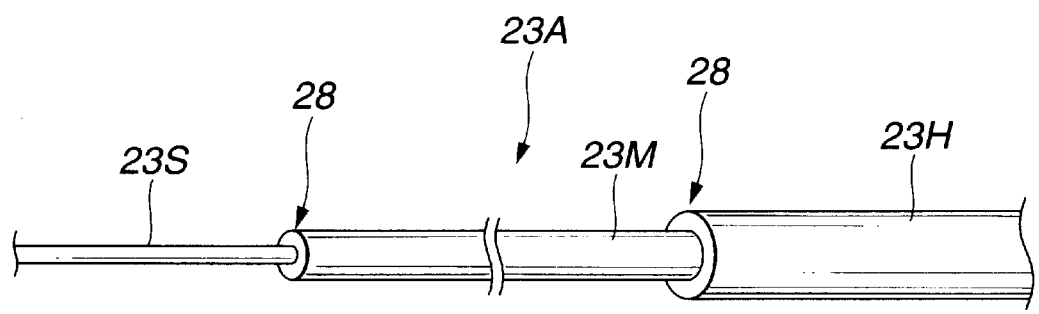
Figure 6:
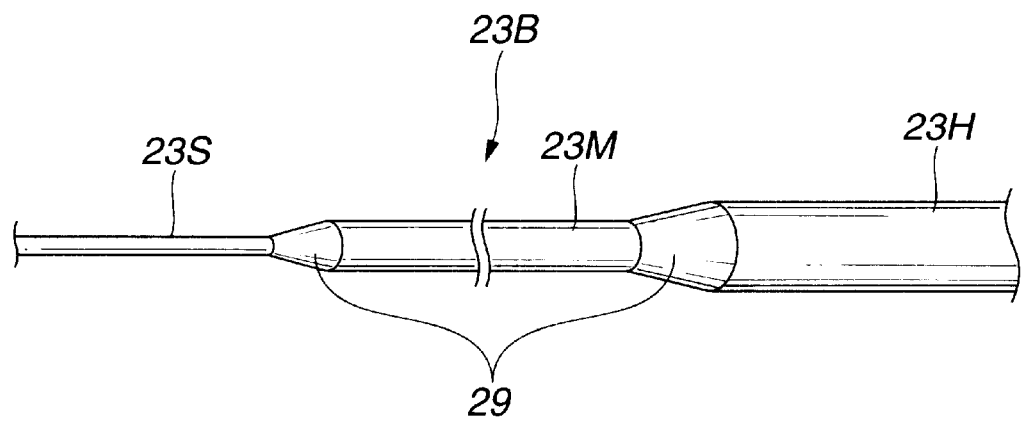

Furthermore, the stilet 23 is not limited to the two-staged type having the soft part of the stilet 23S and the hard part of the stilet 23H in a predetermined area in the longitudinal direction. For example, as shown in FIG. 5, to change the size of the outer diameter to three levels, a middle hardness part 23M having the middle hardness can be created by setting the diameter size to be larger than the soft part of the stilet 23S, but smaller than the hard part of the stilet 23H, for example being expressed by $\phi((d+D)/2)$ in the middle part of the soft part of the stilet 23S and the hard part of the stilet 23H.

With this design, as the stilet 23A has a middle hardness 23M between the soft part of the stilet 23S and the hard part of the stilet 23H of the flexible tube 15, changes in hardness level in a predetermined area in the longitudinal direction of the flexible tube become gentle.

Thus, upon inserting the insertion member 10 into a body cavity, a well-balanced shape of the insertion member is maintained and the torque in the rotational manipulations performed at the proximate part of the insertion member by the operator is reliably conveyed to the distal part to improve the ability to accomplish smooth insertion as well.

Also, the leveled change in a predetermined area in the longitudinal direction of the stilet is not limited to two-levels or three-levels, and a configuration having more levels can be used.

In the stilet 23 and 23A described in the FIG. 4 and FIG. 5, for example, step parts 28 are formed between the soft part 23S and the middle hardness, part 23M as the diameter size gradually changing part in which the hardness level gradually changes. These step parts 28, as shown in the stilet 23 B in FIG. 6, become transition parts 29 as a taper-shaped diameter size continuously changing part in which the diameter size becomes gradually and continuously larger from the distal part to the proximal part. With this design, for example, the hardness change from the soft part of the stilet 23S to the middle hardness part 23M of the stilet 23B becomes gradual, and the hardness change in a predetermined area in the longitudinal direction of the flexible tube 15 becomes gradual as a whole.

With this design, upon inserting the insertion member 10 into a body cavity, the well-balanced shape of the insertion member is maintained and the torque in the rotational manipulations performed at the proximal part of the insertion member by the operator is reliably conveyed to the distal part thereof to further improve the ability to insert smoothly as well.

Figure 7:
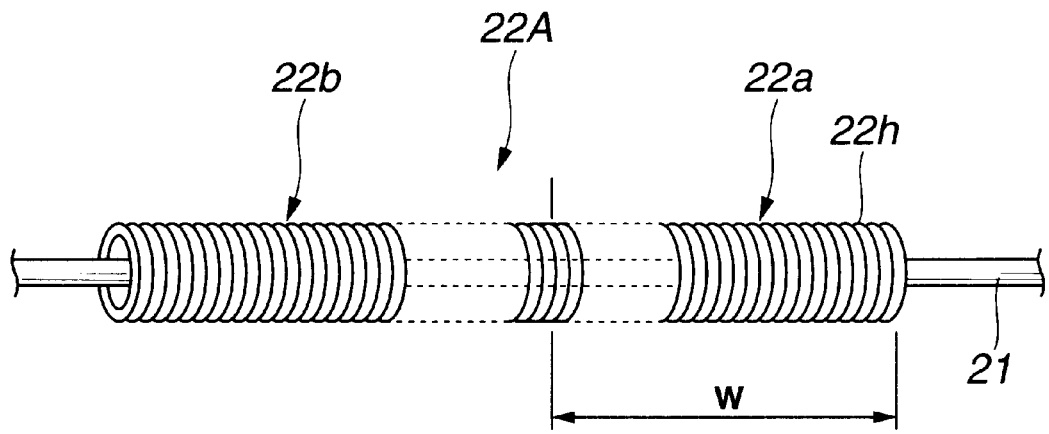
FIG. 7 and FIG. 8 are diagrams for explaining the second embodiment of the present invention.
Figure 8:
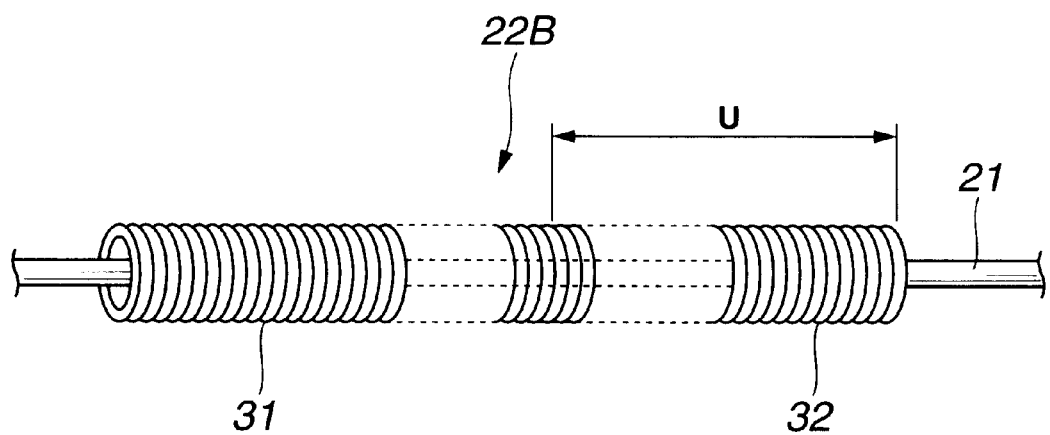

The second embodiment of the present invention is described hereafter, with reference to FIG. 7 and FIG. 8.

In the present embodiment, instead of placing stilet 23, 23A and 23B as the inner parts in the first embodiment to give predetermined properties to the flexible tube 15, and other inner parts, a wire coating coil 22 covering the bending wire 21 is used to provide the predetermined properties to the flexible tube 15.

As shown in FIG. 7, in the wire coating coil 22A of the present embodiment, coating treatment is applied to the proximal part shown as the arrow W in the same FIG. to form a hardening coating (plating) 22h. With this treatment, a coating part 22a, the hard part, and an un-coating part 22b, the soft part, are created in the wire coating coil 22A. In addition, the hardness for bending in the longitudinal direction of the coating part 22a is set to be larger compared with the un-coated part 22b to define the difference in the hardness of the coil as Z. On the other hand, the relationship of Z>X is set between the difference (Z) in hardness of the coil and the difference (X) in hardness of the tube.

In this way, in a predetermined area in the longitudinal direction of a wire coating coil, by forming the coated part and the un-coated part to set a predetermined difference in the hardness of the coil, the hardness for bending in the longitudinal direction of the wire coating coil is altered to compose a flexible tube having a different hardness for bending in the predetermined area of the longitudinal direction without placing a stilet, or regardless of the difference in the hardness of the sheathing tube.

Furthermore, instead of forming a wire coating coil to change the hardness in the predetermined area of the longitudinal direction by the presence or absence of the coating treatment, as shown in FIG. 8, it is possible to combine a first guiding coil 31 forming the distal part and a second guiding coil 32 which forms the proximal part, with a size of U in length, and which is harder than the first guiding coil 31 in composing the wire coating coil 22B.

At this time, the second guiding coil 32 is made of a harder and different material from the material of the first guiding coil 31 or use of a flat coil, for example, having a different sectional shape to increase the hardness for bending in the longitudinal direction.

With the use of the wire coating coil 22B composed by joining more than three guiding coils such as the first guiding coil, the second guiding coil, and the third guiding, hardness change in predetermined areas in the longitudinal direction of the flexible tube 15 becomes gradual.

Also, four of wire coating coils are built into the flexible tube, and all of four wires can have the same configuration. However, the size of W and U can be varied for each wire coating coil. To combine the wire coating coils with different sizes of W and U to place in the flexible tube gives various properties to the flexible tube.

Furthermore, in the embodiment described above, the number of the bending wires 21 is described as four, however the number of the bending wires 21 can be more or less.

According to the present invention, it is apparent that a wide range of different embodiments can be constructed based on the invention without departing from the spirit and scope of the invention. This invention is limited by the appended claims but not restricted by specified embodiments.

What is claimed is:

1. A flexible endoscope, comprising:

a flexible insertion member including a flexible tube, the flexible tube comprising a sheathing outside layer, the sheathing outside layer having a proximal portion and a distal portion in the longitudinal direction of the flexible insertion member, the proximal portion being harder than the distal portion; and a flexibility adjustor placed in the flexible tube and having a proximal portion and a distal portion in the longitudinal direction of the insertion member, the proximal portion being harder than the distal portion, such that an amount of change in hardness level for bending of the proximal portion of the flexibility adjustor and the distal portion of the flexibility adjustor is larger than an amount of change in hardness level for bending of the proximal portion of the sheathing outside layer and the distal portion of the sheathing outside layer.

2. An endoscope according to claim 1, wherein said flexibility adjustor is a stilet made of superelastic alloy.

3. An endoscope according to claim 1, wherein said flexibility adjustor is a stilet made of stainless steel material.

4. An endoscope according to claim 1, wherein the sheathing layer is made using ester thermoplastic elastomer, amide thermoplastic elastomer, styrene resin, olefin resin, fluorine rubber, silicone rubber, or resin of appropriate mixture thereof.

5. An endoscope according to claim 1, wherein the amount of change in hardness level for bending of the sheathing layer includes approximately 0.

6. An endoscope according to claim 1, wherein said flexibility adjustor has a middle part of middle ranged-hardness between the distal portion of the flexibility adjustor and the proximal side of the flexibility adjustor.

7. An endoscope according to claim 2, wherein at least one end of said stilet is latched with a part of the insertion member.

8. An endoscope according to claim 6, wherein said flexibility adjustor is a stilet made of superelastic alloy.

9. An endoscope according to claim 6, wherein said flexibility adjustor is a stilet made of stainless material.

10. An endoscope according to claim 6, wherein the flexibility adjustor has a diameter size gradually changing part in which the diameter size thereof is changed gradually from the distal part of the longitudinal direction to the proximal part.

11. An endoscope according to claim 6, wherein the flexibility adjustor has a diameter size continuously changing part in which the diameter size thereof is changed continuously from the distal part of the longitudinal direction to the proximal part.

12. An endoscope according to claim 1, further comprising:

an operating for bending a bending part provided on the distal portion of the flexible tube, wherein the flexibility adjustor comprises at least one wire coating coil, the wire coating coil has a part with different hardness for bending in the longitudinal direction, coats the operating wire, and guides the operating wire.

13. An endoscope according to claim 12, wherein the wire coating coil comprises a first guiding coil coating said operating wire, and a second guiding coil coating said operating wire and having different hardness for bending from the first guiding coil and connected to the first guiding coil.

14. An endoscope according to claim 12, wherein the wire coating coil has a part to which coating treatment has been applied to form a hardening coating and an uncoated part.

15. An endoscope according to claim 1, further comprising:

operating wires for bending a bending part provided on the distal portion of the flexible tube, wherein the flexibility adjustor comprises wire coating coils, each of the wire coating coils has a part with different hardness in the longitudinal direction, coats each of the operating wires, and guides each of the operating wires, and a part of one of the wire coating coils has different length with respect to a part of at least another one of the wire coating coils.

16. An endoscope according to claim 3, wherein at least one end of said stilet is latched with a part of the insertion member.

* * * * *